(12) United States Patent
Benalikhoudja (10) Patent No.: US 6,405,944 B1
(45) Date of Patent: Jun. 18, 2002

(54) SPRAYING ATTACHMENT AND APPLIANCE (75) Inventor: Karim Benalikhoudja, Vaunavey la Rochette (FR)

(73) Assignee: SARL Prolitec, Perols (FR)

( * ) Notice: Subject to any disclaimer, the term of this patent is extended or adjusted under 35 U.S.C. 154(b) by 0 days.

(21) Appl. No.: 09/486,418

(22) PCT Filed: Aug. 25, 1998

(86) PCT No.: PCT/FR98/01850

§ 371 (c)(1),
(2), (4) Date: Apr. 24, 2000

(87) PCT Pub. No.: WO99/10104

PCT Pub. Date: Mar. 4, 1999

(30) Foreign Application Priority Data

Aug. 25, 1997 (FR) .............................. 97 10598

(51) Int. Cl.$^7$ .............................. A61M 11/06
(52) U.S. Cl. ............... 239/338; 239/71; 239/340; 239/346; 239/351; 239/370; 239/419; 239/434; 239/500; 128/200.18; 128/200.21
(58) Field of Search .................. 239/124, 71, 74, 239/338, 340, 346, 351, 369, 370, 419, 434, 590, 590.3, 590.5, 548, 566, 500, 504; 128/200.14, 200.18, 200.21

(56) References Cited

U.S. PATENT DOCUMENTS

| 2,807,504 A | * | 9/1957 | Bloxsom ..................... 239/338 |
| 2,826,454 A | * | 3/1958 | Coanda ....................... 239/338 |
| 2,869,188 A |   | 1/1959 | Cameto |
| 3,077,307 A |   | 2/1963 | Moore et al. |
| 3,584,792 A | * | 6/1971 | Johnson ................... 239/566 X |
| 4,657,007 A | * | 4/1987 | Carlin et al. ........... 128/200.18 |
| RE33,717 E  | * | 10/1991 | Svoboda ..................... 230/338 |

FOREIGN PATENT DOCUMENTS

| EP | 0608176 | 7/1994 |
| GB | 552689  | 4/1943 |

* cited by examiner

Primary Examiner—Steven J. Ganey
(74) Attorney, Agent, or Firm—Harrison & Egbert (57) ABSTRACT

A nebulizing attachment having a body with an open conical chamber formed therein. The body includes a nozzle with a sharp edge behind which a perforation is formed for supplying air under pressure. Another nozzle is provided in communication with the open conical chamber for supplying liquid therein. The liquid is sucked into the chamber by the effect of vacuum brought about by the passage of the air flow from the nozzle to an outlet therefor. The liquid is fractionated and mixed by the effect of turbulence in this chamber.

4 Claims, 7 Drawing Sheets

SPRAYING ATTACHMENT AND APPLIANCE

TECHNICAL FIELD

The invention presented here involves a nozzle head for the nebulization of liquids having different viscosities, suited to produce liquid particles having dimensions less than 1 μm and to diffuse them in order to form a spray or an aerosol.

The invention presented here also relates to the nebulization device equipped with such a nozzle head.

BACKGROUND ART

Nebulization devices are designed to produce a fine particle spray for the purpose of purification of the atmosphere of place or premises such as premises that are open to the public. In this application, the spray formed can have properties of disinfection, deodorization, and at the same time, the substance sprayed can be a substance that has a smell in order to put a scent in the atmosphere.

Also, substances can be nebulized that have curative properties. Thus, it is known to use this type of device in medical fields such as the veterinary field notably for the treatment of respiratory canals, for vaccination of animals and for the disinfection of farming areas.

Also, these types of devices can also be used in the form of a spray for the formation of a mixture of combustive air with a fuel to supply boilers or even thermal engines.

Other areas of applications of this type of device are also known.

Regardless of the area of application of the device, the results and the efficiencies are even better since the spray is formed from particles having a size that is less than a micron, since the size of the particles is uniform and since the spray has a natural capacity to become diffuse and to become uniformly distributed in the volume in which it is introduced.

Known devices do not allow the known objectives indicated.

In fact, a size of particles that is not constant as well as in the end, a discharge of the large particles, which is manifest in a loss of liquid that can be very costly because of condensation on the surfaces, has been observed with these types of devices.

In order to avoid the discharge of large particles, certain nebulizers require at the outlet special geometric shapes in order to trap the large particles, prohibiting any axial exit of the spray, thus limiting the possibilities of integrating this type of device in assemblies for conveyance and distribution of the spray formed.

In addition, the particles formed with the devices of the prior art have a greater size such that the spray or the aerosol can be transported, without condensation, over great distances, for example, in an air conditioning network or in tubular elements having internal cross-sections on the order of a half-centimeter. These tubular elements can be used in order to transport the spray or the aerosol that is formed towards volumes several dozens of meters away from the nebulization device.

With most of these known devices, it is difficult to nebulize, with acceptable results, liquids having an extensive range of viscosity. In fact, these devices only function correctly for a specified range of viscosity that, moreover, turns out to be very narrow. In addition, this type of device does not offer the possibility for increasing or reducing the rated flow without changing the result.

Finally, the devices planned for the formation of particles having a size less than a micron function using very high air pressure.

The invention presented here has the purpose of solving the known problems mentioned by implementing a nozzle and a device for nebulization that is suitable for producing particles having a size less than 1 μm and to release a spray or an aerosol that is made of particles having a uniform size constant in time that can be transported over relatively sizeable distances without any notable condensation effect in the transporting conduit.

Another purpose of the invention is to implement a nozzle head and a device for nebulization that are suitable to nebulize with the equivalent results, liquids having a very extensive range of viscosity and to do this at different flow rates.

Finally, a last purpose of the invention is to implement a nozzle head and a nebulization device suitable for making particles having a size that is less than a micron under low air pressure in a range of from 0.5 to 8 bars.

SUMMARY OF THE INVENTION

For this purpose, the nebulization nozzle head according to the invention is made of a body in which an open chamber for mixing and fractionation is formed, consisting of an outlet nozzle and in an opposite manner, at the base, a first nozzle behind which a supply hole is made in the body for gas under pressure, an input of the liquid to be nebulized being formed in the body in a manner communicating with the nozzle from the hole, and the input having been connected, by the intermediary of conduits, to a source of gas under pressure and to a reservoir of a liquid to be nebulized, the liquid being sucked into the mixing and fractionation chamber under the action of the partial vacuum created by the passage into it of the gas flow from the first nozzle to the outlet nozzle and being finely fractionated and mixed with the flow of gas under pressure under the effect of turbulences prevalent in this chamber, which has in front of the first nozzle, a spreading section, characterized in that:

the spreading section is formed by a surface of rotation, the spreading section and the zone of the first hole situated immediately upstream from the spreading section are coaxial, the introduction is radial in the direction of the flow of the air across the first nozzle, a third nozzle is formed at the downstream end of the first hole at the level of its intersection with the input of the liquid, the first and third nozzles are both in contact with the liquid input, are set apart from each other, and are formed by the sharp edges and can be aligned axially, the type of the conical jet formed at the outlet of the nozzle head is conical and is made up of fine particles in the center and large particles at the periphery.

According to another characteristic of the invention, the liquid input is formed by at least one cylindrical radial hole terminated by a second formed nozzle and in the mixing and fractionation chamber and in the first hole (8), the geometrical longitudinal axis of symmetry from the zone of the second hole, located immediately upstream from the second nozzle is contained in the geometric plane containing the first nozzle which is defined by a sharp edge formed by the intersection of the spreading section with the upstream zone of the first hole.

the longitudinal axis of symmetry of the zone of the second hole located immediately upstream from the second nozzle is secant and perpendicular to the axis of symmetry of the spreading section.

Using these devices, at the output of the nozzle head, a conical jet is obtained which is made of fine particles having a size less than a micron, in a large number, and larger particles that are larger and thus heavier, in a reduced number.

The characteristics of the nozzle head make it so that a mixture of these particles is obtained that is non-homogeneous; the heaviest particles are located in the peripheral zone of the conical jet while the particles that are finer, and thus lighter, are located in the central zone.

Thus, already at the outlet of the nozzle head for nebulization and due to the characteristics of this nozzle head, the separation between the large particles to be extracted from the spray and the fine particles is done before the spray is formed.

In order to further improve this result, the spreading section extends evenly from the first nozzle to the outlet nozzle, i.e. over the entire length of the mixing and fractionation chamber, and it preferably has the shape of a truncated cone whose angle to the peak is made in a range from ten to ninety degrees. Excellent results have been obtained with an angle to the peak equal to sixty degrees. It goes without saying that these values are only given as a rough guide; the angle to the peak can be less than ten degrees or greater than ninety degrees.

The length of the chamber can be limited to a few millimeters, for example, to six millimeters, this length being sufficient in order to form a turbulence zone of sufficient size in order to ensure the separation of the particles.

It is noted that the turbulences are created essentially at the level of the two nozzles for the input of the liquid and compressed gas, due to the irregularity of the surface that is present at this level and due to the sharp edge that demarcates the nozzle from the compressed gas input.

Another factor that contributes to the creation of the turbulences is the imbalance of the jet formed, i.e. its offset relative to the axis of symmetry of the spreading section, this offset being due essentially to the presence of a unique nozzle for the liquid input.

In order to improve the flow rate while maintaining this imbalance, the invention, according to another of its characteristics, provides several second nozzles distributed in an irregular manner around the axis of symmetry of the mixing and fractionation chamber.

As a variation, a regular distribution can be provided, but with nozzles having different diameters.

According to another characteristic of the invention, the zone of the first hole, located immediately upstream from the first nozzle, and the zone of the second hole, located immediately upstream from the second nozzle, are both cylindrical. Moreover, the zone of the first hole, located immediately upstream from the first nozzle has a diameter that is smaller than the diameter of the zone of the second hole, located immediately upstream from the second nozzle.

Purely as a rough guide, these zones have diameters that are roughly equal to 400 $\mu$m and to 800 $\mu$m, respectively. It goes without saying that these values are only given purely as a rough guide, the respective values of the diameters of the two zones can be less than or greater than the values indicated.

By these relatively standard dimensions in the field of precision mechanics, it is thus possible to create nozzles fitted to create particles less than 1 $\mu$m and this is done with the manufacturing tolerances standard in this field.

This is due to the fact that producing particles all having a size less than a micron at the output of the nebulization nozzle head had not been researched essentially with a view to efficiency and simplification of the creation, but on the contrary, unpredictably producing fine particles and coarse particles. The only requirement was that the fine particles that have dimensions less than a micron be sufficient in number in order to form a sufficiently dense spray in order to be used.

In order to greatly reduce the number of the large particles in the jet emitted by the nebulization nozzle head, according to another characteristic of the invention, above the outlet nozzle, at a distance from it, a deflector plane is mounted, where this deflector is perpendicular to the axis of symmetry of the chamber and centered relative to it. The deflector has a length and width greater than the diameter of the nozzle at the output and being notably designed to turn down the jet laterally towards the edge forming the nozzle at the outlet of the mixing chamber. This device makes it possible to create at this level, i.e. on the outlet nozzle, a fractionating of the large particles. In order to reinforce this result, the outlet nozzle is formed by a sharp edge. If desired, the deflector is designed to catch and deflect the large particles.

The size of the particles formed depends closely on the distance between the deflector and the nozzle of the outlet. As a guideline, this distance will be greater than 5 $\mu$m and can be between 100 $\mu$m and 5 mm. Depending on the case, the distance between the deflector and the outlet nozzle can be fixed or even adjustable in order to regulate the size of the particles emitted and to adapt the spraying nozzle head to the viscosity of the liquid to be nebulized. The distance between the deflector and the outlet nozzle determines the flow rate of the nebulization. In an unexpected manner, a low distance corresponds to a sizeable flow rate.

Excellent results have been obtained with a distance of 150 $\mu$m.

Finally, the nebulization nozzle head, according to another embodiment form, can be provided with a hole planned for the vacuum extraction of residual flows, this second hole opening on the one hand, into the mixing and fractionation chamber and on the other hand, on one of the sides of the body of the nozzle head where it forms at this level a vacuum extraction opening of the residual flows of the liquid formed by the large particles.

The different characteristics of the nebulization nozzle head such as the ones that have just been listed allow nebulization with identical or at least, comparable, results for liquids having viscosities that are very far apart such as aqueous solutions and oils and this is done under a range of gas pressure and thus of flow rate, which as far as it is concerned is very extensive, for example, pressures from 0.5 bars to 8 bars.

In addition, the reduced length of the fractionation and mixing chamber from the nebulization nozzle head makes it possible to produce an effective response to the dimensional restrictions posed by the implantation in the devices of nebulization having a reduced size.

The nebulization device according to the invention is characterized essentially in that it is equipped with at least one nebulization nozzle head as described above.

This device, according to another characteristic, consists of a hollow body at the base of which and in which at least one nebulization nozzle head is mounted relative to on the one hand, a source of compressed gas by the intermediary of a conduit and on the other hand, with a reservoir of a liquid to be nebulized, mounted under the body, where the nebulization nozzle head, by its outlet nozzle, is in communication with an expansion chamber made in the body of the device, coaxial to the mixing and fractionation chamber of the nebulization nozzle head, the internal side of the chamber receiving the large particles emitted by the jet and catching them, so that they flow under the action of their weight on this side, towards the reservoir.

When the nozzle head is equipped with the deflector, the nebulized jet is caused to spin around in the expansion chamber. This is due to the sloped surface of the nozzle head whose main role is to conduct and direct this jet.

The jet of particles emitted by the nebulization nozzle head, as far as the peripheral zone of it is concerned, i.e. the one formed by the large particles, is oriented towards the inner side of the expansion chamber in a manner such that the large particles are caught by it.

According to another characteristic of the invention, the expansion chamber as opposed to the nebulization nozzle head, is limited by a transverse wall perpendicular to the geometric axis of the fractionation chamber, this wall contains in its center a hole that passes through the nebulization outlet. The height of this transverse wall relative to the spraying nozzle head as well as the diameter of hole passing through can vary as a function, for example, of the physical characteristics of the liquid to be sprayed.

According to yet another characteristic of the invention, the external side of the nebulization chamber, of the transverse wall, is convex and this wall consists of indentations on its periphery. This arrangement allows the flow towards the expansion chamber of any condensate formed above or on the transverse wall.

The inner side of the expansion chamber can be smooth, or even be equipped with one or more projections or hollows.

However, to the extent the configuration of the inner side of the chamber is smooth or has relief, it leads to a loss of a sizeable load.

From this loss of load, a drop in the speed of the progression of the spray of micro-particles results in the device, along with a risk of deposit and condensation, over time, of these micro-particles on the inner side of the body and as a consequence, a risk of driving the particles having a larger size into the jet of micro-particles.

In order to compensate for this disadvantage, according to another characteristic of the invention, the expansion chamber is extended by at least one acceleration zone of movement of the spray of particles in order to increase the speed of the spray and avoid any deposition of fine particles, the aforementioned zone being in contact with an outlet conduit of the spray or the aerosol formed.

The speed of the particles in the acceleration zone is sufficiently sizeable in order to prevent them from being caught and condensing against the walls of the hollow body.

In the preferred embodiment form, the acceleration zone of movement of the spray is in contact with the expansion chamber by a passage having a smaller cross-section than the cross-section of the chamber, this passage having a smaller cross-section can be formed, when the expansion chamber is limited by the transverse wall, by the hole passing through the wall.

This passage having a reduced cross section is favorable itself on the outlet, to emit a jet at an increased speed.

According to another embodiment form of the invention, the expansion chamber, as opposed to the nebulization nozzle head, contains a blockage wall and the wall of the reservoir, and above the maximum level of the liquid, is equipped with an outlet nozzle of the spray or aerosol. This embodiment form, which no longer provides the upper acceleration zone, enables the creation of a particularly compact device.

According to another characteristic of the invention, the body of the device, between the reservoir and the expansion chamber, is equipped with a transversal partition that carries the nebulization nozzle head. This partition, for a device equipped with an upper acceleration zone, ensures the air-tightedness between the expansion chamber and the zone of the reservoir located above the level of the liquid. This device prevents that under the effect of the pressure, the spray of particles is led towards the bottom and into the reservoir, which would weaken the efficiency of the device as a consequence.

For a device whose spray or aerosol outlet is guided into the wall of the reservoir, the partition will be equipped with a communication opening of the expansion chamber with the volume of the reservoir located above the level of the liquid.

According to another characteristic of the invention, the nebulization device is equipped with a mechanism for evacuation towards the reservoir the residual flows of the liquid formed by the large particles in the expansion chamber. This device prevents blocking of the expansion chamber by the flows.

According to another characteristic of the invention, the evacuation mechanism of the residual flows towards the reservoir passes through both sides of the partition. This mechanism, by its lower end, is located below the minimum level of liquid in the reservoir. This device, which provides a mechanism for the internal evacuation of the device, also leads to a better compactness of the device.

For a device whose expansion chamber is separated in an airtight manner from the zone of the reservoir located above the level of the liquid, the evacuation mechanism towards the reservoir, of the residual flows of liquid formed by the large particles, is made up of at least one tube engaged in a hole made in the transverse partition, where the partition and the tube ensure more separation between the volume of the reservoir located above the level of the liquid and the expansion chamber.

For a device whose expansion chamber is in communication with the zone of the reservoir located above the level of the liquid, the evacuation mechanism is made up of a blade engaged in the communication opening.

For a device equipped with a transverse partition ensuring the airtight separation between the expansion chamber and reservoir for the liquid to be nebulized, it is also possible to prevent the blocking of this chamber by the accumulation of residual flows using a nebulization nozzle head equipped with a vacuum extraction hole opening on one of the sides of the body of the nozzle head.

BRIEF DESCRIPTION OF THE DRAWINGS

Other goals, advantages and characteristics of the invention appear in reading the description of the preferred embodiment forms given as non-restrictive examples in referring to the attached drawings, in which.

DETAILED DESCRIPTION OF THE INVENTION

Figure 1:
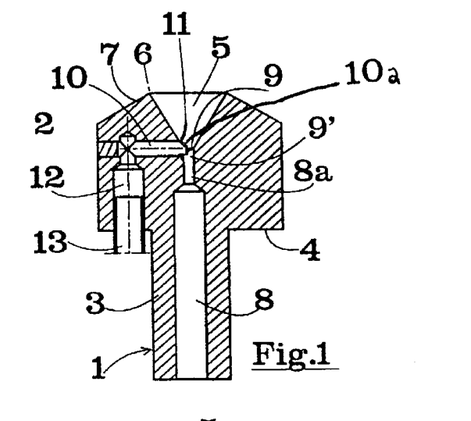
FIG. 1 is a view in a longitudinal section of a nebulization nozzle head according to a first embodiment form.

FIG. 1 shows a nebulization nozzle head 1 according to a first embodiment form of the invention.

This nozzle head includes a body formed from two cylindrical forms 2, 3 axially aligned, having different diameters, separated from each other by a shouldered surface 4, the diameter of the cylindrical form 3 being less than the diameter of the cylindrical form 2. Along the longitudinal axis of the body, in the cylindrical form 2, from the front side of it, a mixing and fractionation chamber 5 is made using any known methods, in the form of an inverted truncated cone, the large base of the truncated cone being located in the front side and being limited by a sharp circular edge that forms the outlet nozzle 6 of the nozzle head 1. Preferably, the outlet nozzle 6 is contained in a plane that is normal to the axis of symmetry of the chamber 5. Around the outlet nozzle 6, the body of the nozzle head has a sloped surface 7 that forms a truncated cone. This sloped surface, in allowing the flow of the large particles towards the base where they accumulate, prevents them from being guided into the jet. In the axis of the mixing and fractionation chamber 5, the second cylindrical form 3 is passed through on both sides by a hole 8, or first hole. This hole opens into the mixing and fractionation chamber 5 in order to form there, following the small base of the truncated cone shape of this chamber, a first nozzle 9 defined by a sharp edge and contained in the geometric plane perpendicular to the longitudinal axis of symmetry of the chamber 5. The hole passing through 8 ends immediately upstream from the nozzle 9 with a zone 8a having a smaller diameter, on the order, for example, of 400 µm, and the diameter of the first nozzle 9 is equal to this value. The length of the zone 8a determines the range of functioning pressures, i.e. the pressure of the gaseous fluid upstream from the hole 8. Thus, with a length of 5 to 6 mm, the functioning range consists of between 0.5 bars and 3.5 bars, with a length of 2 mm it consists of between 2 and 6 bars. Below the minimum values, the Venturi effect does not occur. Above the maximum values, the nebulization no longer occurs; a part of the gaseous fluid rushes into the input 10 of the liquid and pushes the liquid back towards the reservoir.

The second cylindrical form 3 forms a channel and is designed to be connected by a conduit to a source for the distribution of gas under pressure. This gas can be air.

According to the geometrical plane of the first nozzle 9, the first cylindrical form is provided in a radial cylindrical hole 10 whose longitudinal axis of symmetry is radial to the first nozzle. This second hole opens into the mixing chamber and into the zone 8a of the first hole and forms at this level a second nozzle 11 extending on both sides of the geometric plane of the first and a third nozzle 9' resulting from the intersection of the cylindrical surface of the second hole with the cylindrical surface of the first hole. Immediately upstream from the second hole 11, the radial hole 10 has a zone having a lower diameter 10a, the value of the diameter of this zone being, for example, on the order of 800 µm. As opposed to the nozzle 11, the radial hole 10 is blocked by an appropriate stopper. As an example, this stopper will be threaded and engaged in a tapped hole made in the radial hole. From the shouldered side, a supply hole 12 opening into the hole 10 is made in the first cylindrical form, parallel to the longitudinal axis of it. In this hole 12, from the shouldered surface 4, a threaded countersinking is made into which the threaded end of a vacuum extraction tube 13, of a liquid to be nebulized, can be screwed.

By passage of the compressed air from the nozzle 9' to the nozzle 9, at the level of the nozzle 11, a partial vacuum is created under the action of which if the speed of the compressed air is sufficiently high, the liquid to be nebulized is vacuum extracted in the tube 13 as well as in the holes 12 and 10 in order to reach the nozzle 9 and then fractionate and mix with the air flow in the truncated cone spreading section that forms the chamber 5.

This nebulization nozzle head as described emits at the outlet a spray in the form of a conical jet that contains the large particles in the peripheral zones and particles having a size less than 1 µm in the central zones.

Figure 2:
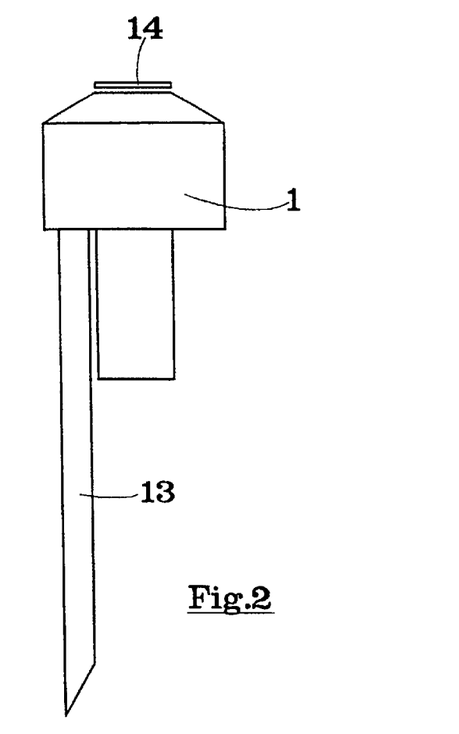
FIG. 2 is a side elevational view of the nebulization nozzle head of the first embodiment of the present invention.

In FIG. 2 you can see that the nebulization nozzle head according to the invention is equipped with a deflector 14 that appears, for example, in the form of a rectangular planar blade that has length and width greater than the diameter of the outlet nozzle. This deflector 14 is parallel to the plane of the outlet nozzle 6 and is maintained in a centered manner relative to the longitudinal axis of symmetry of the chamber 5. In addition, in order to allow the adjustment of the size of the particles and the emission of particles having sizes fitted to the planned application, the distance between the deflector 14 and the outlet nozzle is controllable. A low distance, on the order of a dozen millimeters, corresponds to the formation of fine particles due to the increase of turbulence in the chamber which supports the fractionation, while a large distance on the order of a half-centimeter corresponds to a reduction of the size of the turbulence in the chamber, and thus less fractionation of the particles.

Figure 4:
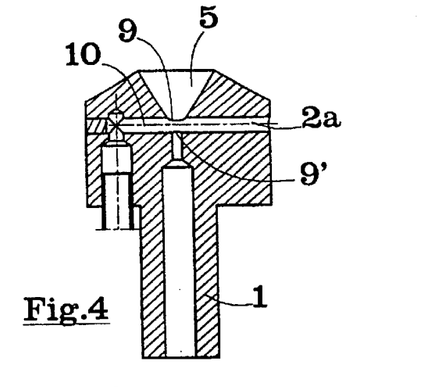
FIG. 4 is a sectional view of a nebulization nozzle head with a radial hole for the vacuum extraction of the residual flows.

The nebulization nozzle head, as just described, can be equipped as seen in FIG. 4, with at least one radial hole 2a opening on the one hand, in the mixing and fractionation chamber 5 and on the other hand, on the cylindrical face of the first cylindrical form 2 of the body of the nozzle head where it forms at this level a vacuum extraction opening for the residual flows of liquid formed by the large particles. Thus, any accumulation of residual flow is vacuum extracted in the nozzle head in order to undergo nebulization again in the fractionation chamber 5.

Figures 3, 4A:
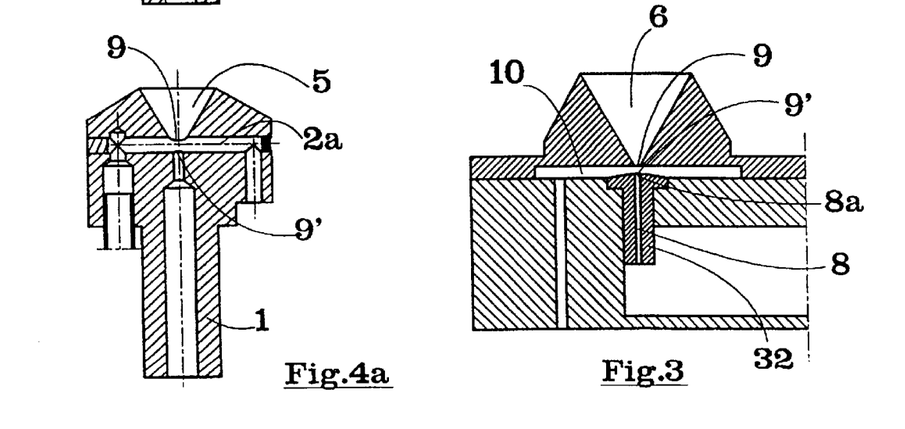
FIG. 3 is a sectional view of a nozzle head according to another embodiment form.
FIG. 4a is a sectional view of a nebulization nozzle head with a radial hole for the vacuum extraction of the residual flows according to a second embodiment form.

As a variation, as shown in FIG. 4a, the hole 2a that has a vertical part in order to not open into the cylindrical face of the first cylindrical form of the body of the nebulization nozzle head but into an indentation that it has in the lower part. According to this embodiment form, the vacuum extraction of the residual flows occur from the indentation.

Shown in FIG. 3 is a nozzle head according to another embodiment form. You can see that the input 10 of the liquid extends between and around the nozzles 9 and 9', where they are preferably set off at a distance by a value of a few dozen millimeters. Preferably, without being restrictive, the nozzles 9 and 9' each of which are always defined by a sharp edge, have the same diameter. This nozzle head is made of a body in two parts assembled to each other in a manner so that they can be disassembled. The mixing and fractionation chamber 6 as well as the input 10 are formed in the first part of the body while the second part of the body is equipped with the first hole 8 and conduits connecting the hole 8 and input 10 to the source of the gas under pressure and to the reserve of the liquid to be nebulized. Preferentially, the input 10 is made up of a cylindrical chamber arranged at the base of the first body of the nozzle head. During the assembly of the two parts of the body of the nozzle head, the cylindrical chamber is positioned relative to a surface junction plane that contains the second part of the body of the head. Always depending on the preferred form of the invention, the hole 8 is formed in a detachable nozzle 32 introduced into a housing of the second part of the body, formed in a manner passing through from the surface junction plane to a blind passage connected by any appropriate means to the source of the compressed gas. This detachable nozzle as can be seen in FIG. 3 includes a cylindrical nozzle head housed in a countersink of the housing. The head of the nozzle contains around the nozzle 9' a sloped surface in a truncated cone that forms a projection on the surface of the junction. You can notice that the cylindrical surface of the head is completely housed in the countersinking, the only projecting shape is the sloped surface. This arrangement makes it possible to guide the liquid to be nebulized to the compressed air flow passing from the nozzle 9' to the nozzle 9.

Figure 5:
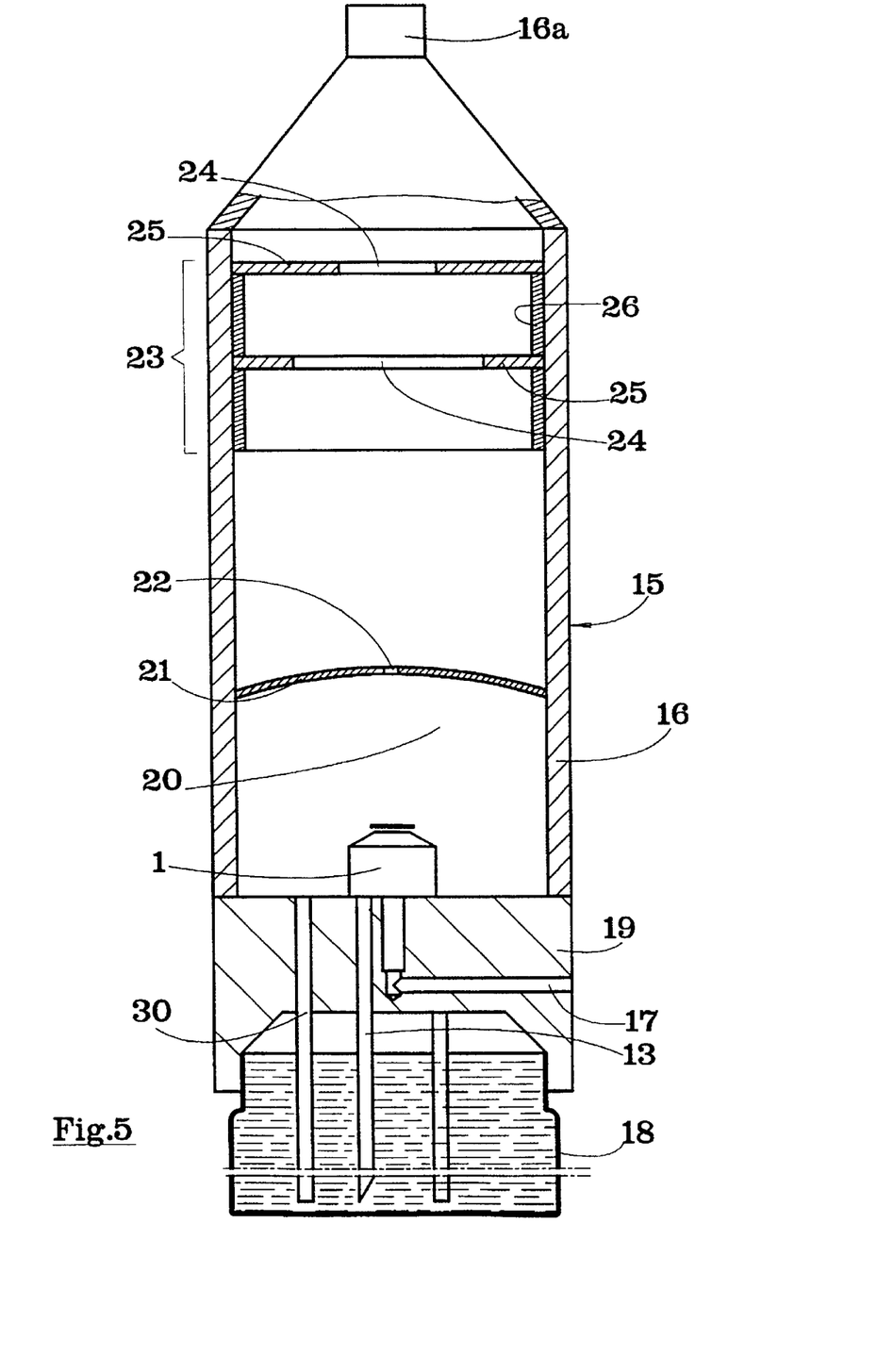
FIG. 5 is a longitudinal sectional view of a device according to a first embodiment form.
Figures 6, 7:
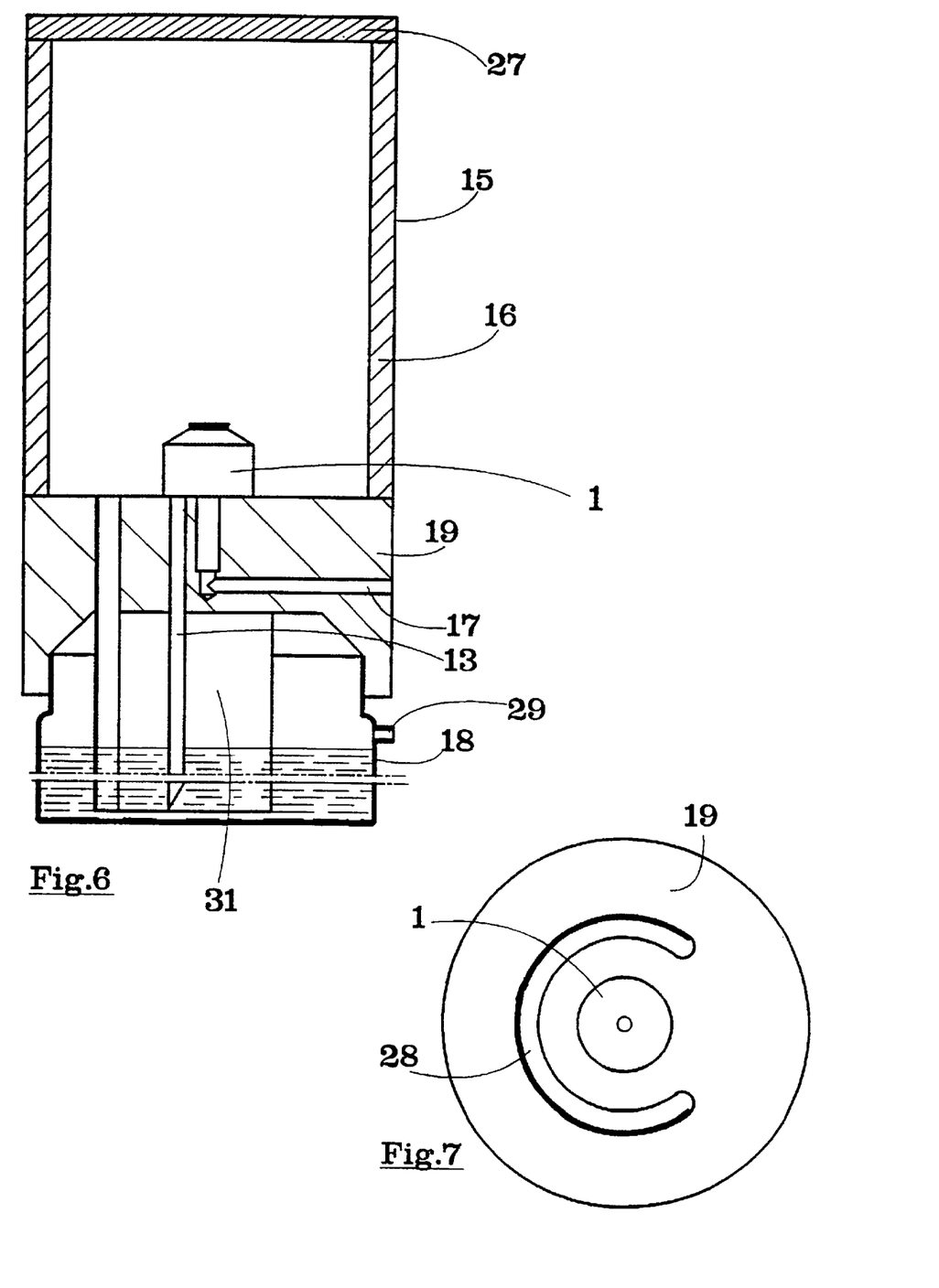
FIG. 6 is a longitudinal sectional view of a nebulization device according to a second embodiment form.
FIG. 7 is a plan view of the nebulization device of FIG. 6.
Figure 8:
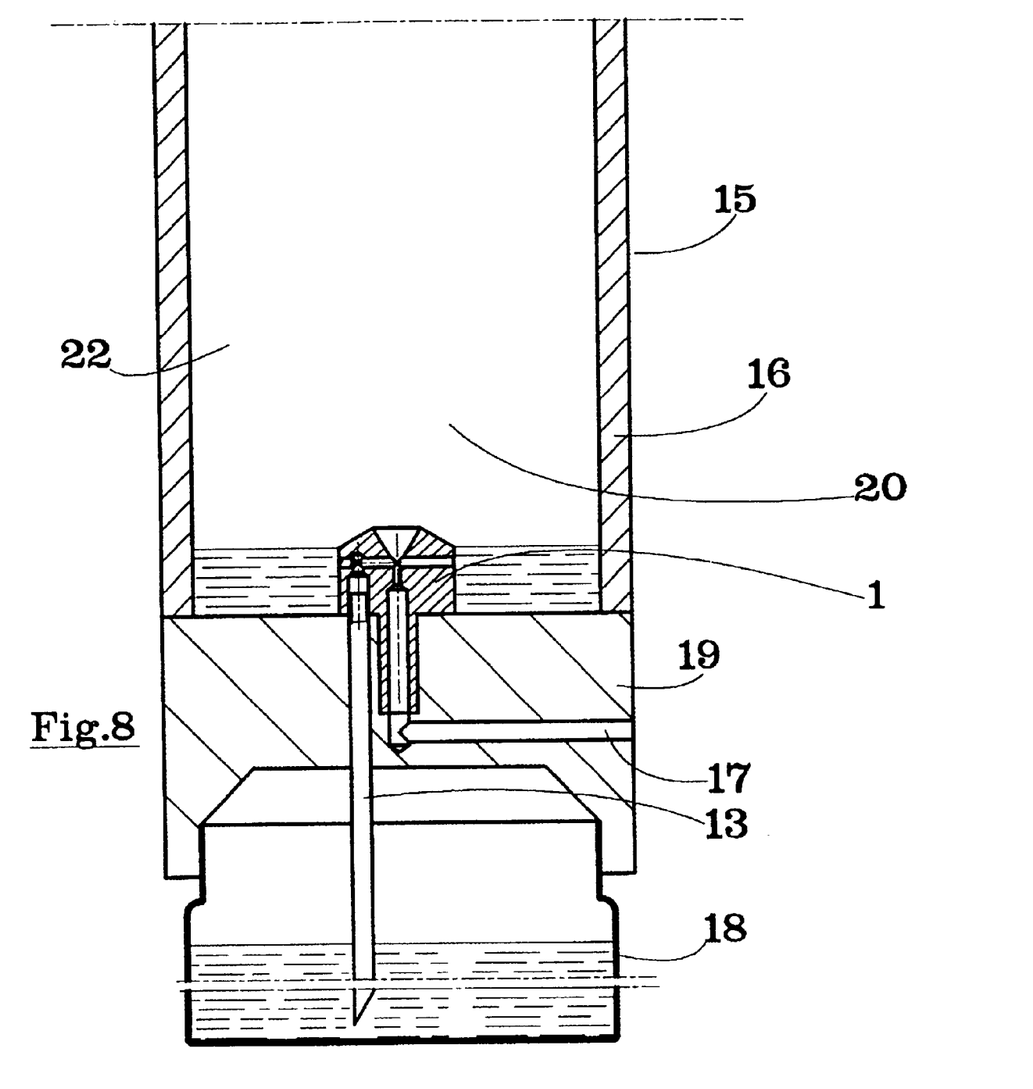
FIG. 8 is a sectional view of a device according to a fourth embodiment form.
Figure 9:
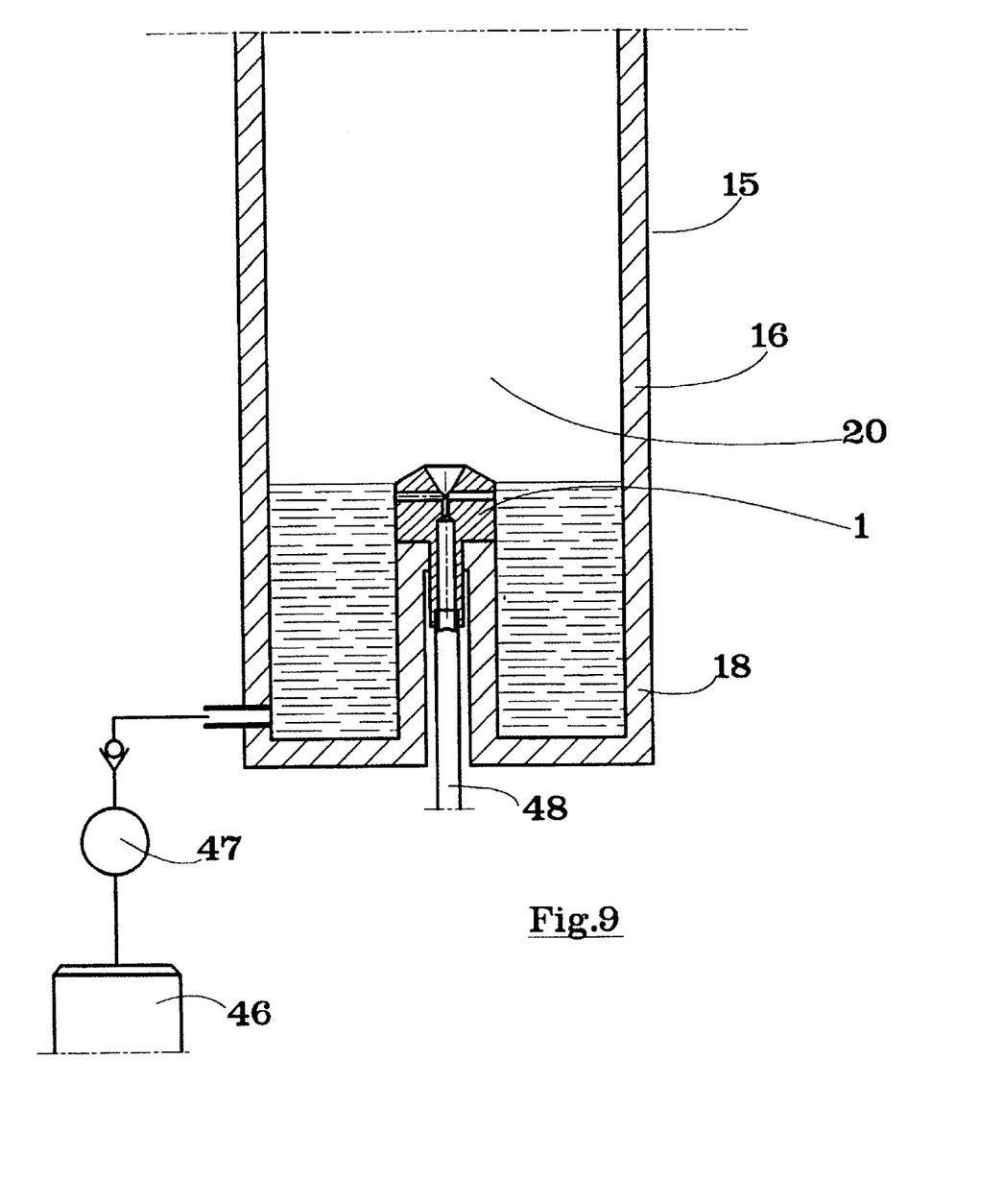
FIG. 9 is a sectional view of a device according to a fifth embodiment form.
Figure 10:
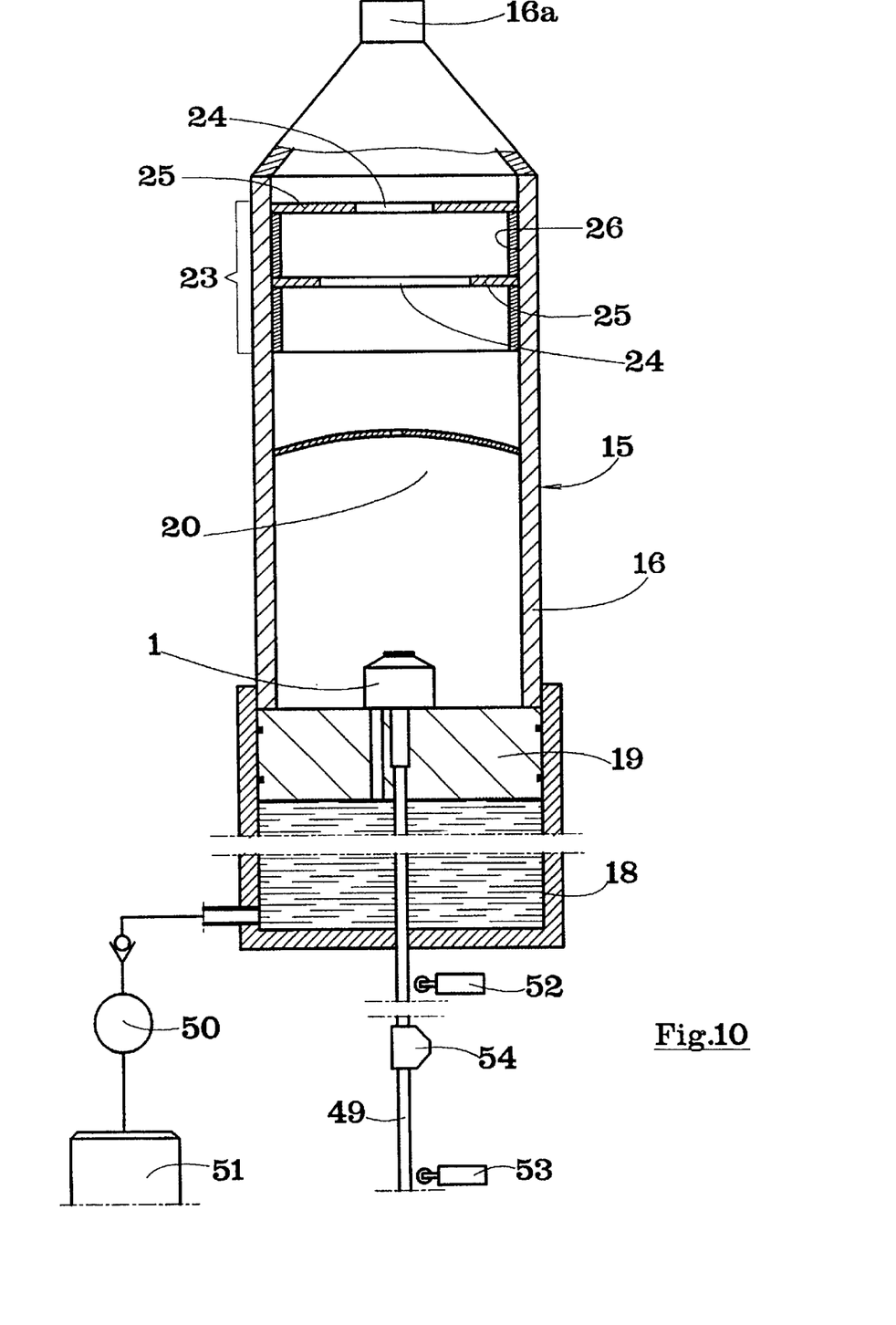
FIG. 10 is a longitudinal sectional view of a device according to a sixth embodiment form.

FIG. 5 shows a nebulization device 15 according to a first embodiment form.

This device contains at least one nebulization nozzle head 1 according to one type of embodiment and containing a hollow body 16 at the base of which at least on nebulization nozzle head 1 is mounted that is supplied with compressed gas, for example, air, by a conduit 17 connected to a source of compressed gas. The nozzle head is supplied with liquid to be nebulized by the vacuum extraction tube 13, this tube sticking into the liquid reservoir 18 mounted under the body 16 and separated from it by a transverse partition 19 that supports the nebulization nozzle head 1. The jet of particles produced by the head 1 is admitted into the expansion chamber 20 formed in the body, above the transverse partition 19. As opposed to the nebulization head, the body of the device is equipped with a hole passing through, tapped in which is engaged the threaded tip of an outlet tube **16*a*** of the particle spray.

In the preferred embodiment form, the expansion chamber 20 is in a cylindrical shape but as a variation, the form of the chamber can be parallelepiped. The expansion chamber 20 and the mixing and fractionation chamber 5 of the nebulization nozzle head are coaxial with respect to each other. Always according to the preferred embodiment form, the partition 19 is provided with a nozzle passing through and a blind nozzle that are parallel to each other, the blind nozzle being made in the wall 19 from the side turned toward the expansion chamber. In these nozzles, with the interposition of toroid airtight seals, on the one hand, the vacuum extraction tube 13 and on the other hand, the second cylindrical shape 3 of the body of the nozzle head are respectively engaged. The blind nozzle is in communication with a radial hole made in the transverse wall from the outside of the body of the device. This radial hole is in communication with a conduit (not shown) connected to a source of compressed air in order to ensure the supply of the nebulization nozzle head with compressed air.

The expansion chamber 20 is preferably defined by the internal volume of the body of the device.

Preferably, the expansion chamber 20 in contrast to the nebulization nozzle head 1 is defined by a transversal wall 21 perpendicular to the geometric axis of the fractionation chamber of the nozzle head, where this wall at its center contains an opening 22 that passes through the nebulization outlet.

Advantageously the outer side of the nebulization chamber, of the transversal wall 21 is convex and contains indentations in its periphery. This arrangement allows the gravitational flow, towards the expansion chamber and towards the reservoir, of possible liquid condensates formed above the wall or even on the convex side.

In the embodiment form that is shown in FIG. 5, the expansion chamber 20 is extended axially towards the outside by a zone 23 for accelerating the movement of the spray of particles in order to increase their speed and prevent any deposition of the particles on the sides of the inside volume of the body of the device.

According to a preferred embodiment, the acceleration zone 23 is connected to the expansion chamber 20 by a passage 24 having a smaller cross-section than the cross-section of the chamber. This passage 24 is made, for example, by a hole that passes through and is formed in a partition 25 extending transversally in the hollow body and held fixed in the body against the upper edge of the tubular sheath **20*a* or at a distance from it. This hole 24 passing through can be formed by an oblong aperture but any other form of the hole could be appropriate. Advantageously the acceleration zone consists of at least two partitions 25 with openings going through them, mounted at a distance from each other, the opening passing through one being shifted angularly by ninety degrees relative to the opening passing through the other one in order to make the jet undergo a rotation between the two partitions by a quarter turn, which increases the tangential speed of the particles and reduces the risk of agglomeration of these particles on the sides of the inner volume of the body of the device. These partitions 25 can be kept at a distance from each other on the hand, and at a distance from the sheath 20*a* on the other hand, by a set of several tubular distance sleeves 26** mounted in the inner volume of the body of the device.

The nebulization device according to FIG. 6 is no longer equipped with the upper acceleration zone arranged above the expansion chamber 20 and this expansion chamber, in contrast with the nebulization nozzle head 1, has a blocking wall 27 affixed in a known manner in itself at the upper edge of the tubular sheath **20*a*. According to this variation, the transversal partition 19 is provided with an opening 28 for communication of the expansion chamber 20 with the volume of the reservoir located above the level of the liquid and the wall of the reservoir 18, above the maximum level of the liquid, is equipped with a tapped hole into which the threaded tip of an outlet conduit 29, for the spray or aerosol formed, can be screwed. The communication opening 28 will be arranged in the partition 19 around the body of the nebulization nozzle head 1** according to a circumferential circular arc.

Preferably, the nebulization device, according to one or the other embodiment form as described, is equipped with a mechanism for evacuation towards the reservoir, of the residual flows of the liquid formed by the large particles in the expansion chamber: preferably, this mechanism passes straight through the partition and comes at its lower end below a minimum level of the liquid in the reservoir.

For the device according to FIG. 5, the evacuation mechanism consists of at least one vertical tube 30 engaged at its upper end in a hole passing through that is made in the partition 19, this partition 19 and the tube 30 ensuring in addition the airtight separation between the volume of the reservoir located above the level of the liquid and the expansion chamber. By its lower end, the tube 30 comes below the minimum level of the liquid in the reservoir 18. For a complete evacuation of the residual flows, several holes passing through, which are each connected to an evacuation tube appropriate for them, can be provided in the partition 19, around the body of the nebulization nozzle head.

For the device according to FIG. 6, the evacuation mechanism will be made up of a vertical blade having a small thickness, engaged at its upper end in the communication opening and pinned against one of the longitudinal edges of the opening completely covering it. The residual liquid in sliding over this blade is conducted by dripping down towards the reservoir 18 and the liquid contained in it.

FIG. 8 shows in a partial manner a nebulization device whose nebulization nozzle head is equipped with a hole 2*a* for vacuum evacuation of the residual liquid. This hole can open in the cylindrical side of the first cylindrical form of the body of the nozzle head or even a variation, as shown in FIG. 4*a*, having a vertical part in order to open into an indentation arranged in the first cylindrical form. According to one or the other of these two embodiment forms, the device is equipped with a partition 19 that ensures an airtight separation between the reservoir in its assembly and the expansion chamber. The device according to this embodiment form is not equipped with a mechanism for evacuation to the reservoir of the residual flows, which simplifies its creation.

In FIG. 9 a nebulization device is shown that is free from the partition 19. In this embodiment form, the inside volume of the reservoir is directly in communication with the expansion chamber 20 and contains projecting on its base a cylindrical protuberance supporting the nebulization nozzle head 1. The nebulization nozzle head 1 does not contain a supply hole and the radial hole 12 now opens onto the cylindrical side of the first cylindrical form-of the nozzle head 1 in order to form at this level a nozzle located above the level of the liquid in the reservoir. This nozzle head can also be equipped with a hole for vacuum extraction of the residual liquid, which opens either in the cylindrical side of the first cylindrical form of the body of the nozzle head, or in an indentation formed on the lower part. Moreover, the hole 12 can contain a vertical part and not open in the cylindrical surface of the first cylindrical form of the body of the nozzle head, but in an indentation formed in the lower part of the body of the first cylindrical form of the body of the nozzle head.

The device is connected to the mechanisms to keep constant the level of the liquid in the reservoir, these mechanisms can includes a storage capacity 46 of the liquid to be nebulized, outside of the device and of a pump 47 whose extraction opening is connected by an appropriate conduit to the internal volume of the storage capacity. By the intermediary of an appropriate conduit, the delivery opening of the pump is connected to the inside volume of the reservoir 18. The flow rate of the pump can be fixed to the flow rate of the nebulized liquid or even the sensors of the level, not shown, connected to a control circuit for starting or stopping the function of the pump 47, can be arranged in the reservoir. In this embodiment form, the residual of the liquid falls directly back into the reservoir 18. According to this embodiment form, the nebulization nozzle head is supplied with compressed air by a vertical channel 48.

In order to prevent the presence of the sensor at the level in the liquid reservoir, a device can be provided with a partition 19, mounted in a manner sliding in the reservoir like a piston. In this embodiment form, as shown in FIG. 10, the device 15 contains an external cylindrical surface and slides with a little play, by this cylindrical external surface, in the cylindrical bore of the reservoir 18. The lower part of the body of the device and more particularly the partition 19 is constructed as a piston and contains one or more annular, airtight segment(s). According to this embodiment form, the supply of compressed air is no longer carried out by a radial opening made in the partition 19, but by a rigid cannula 49, in communication with the hole 8 of the body of the nebulization nozzle head by the intermediary of an axial hole passing through, made in the partition 19. This cannula 49 extends into the reservoir 18 along the direction of the sliding of the body of the device and is engaged in sliding in a bore made in the wall of the base of the reservoir. Airtight annular seals are arranged in the bore in order to avoid any leakage of the liquid at this level. On the outside of the reservoir, the cannula is connected by a flexible conduit to a source for the distribution of air under pressure. The device according to this embodiment form is carried along by the liquid present in the reservoir 18. Thus, the degree to which the body of the device is pushed into the reservoir depends on the quantity of the liquid contained in it. Due to this fact, by the measure or the detection of the degree to which it is pushed in, it is possible to detect the quantity of liquid in the reservoir and if the level is very low, to restock the liquid in an automatic manner with the help of a pump 50 that has an opening for pumping out the liquid. The opening is connected by an appropriate conduit to the internal volume of a liquid reserve 51. The delivery opening this pump is connected to the internal volume of the reservoir 18 by the intermediary of an appropriate conduit. This pump 50 will be activated by an electric motor, controlled by a circuit that has automatic functioning and power, containing notably outside the reservoir 18, two sensors at the level 52, 53 at a distance from each other and both arranged in the path of an activation contact 54 carried by the cannula. The sensor closest to the reservoir or the first sensor, emits when it is activated a signal representing a maximum level of the liquid in the reservoir 18, while the second sensor emits when it is activated a signal representing a minimum level of the liquid. The application of the latter signal on the corresponding input of the automatic functioning and power circuit commands the closing of the supply circuit of the electric motor for activating the pump and thus the activation of the pump 50. The pump then pumps out the liquid contained in the reserve 51 and delivers it to the reservoir 18. The liquid introduced progressively pushes back the device 15 to its position of being set back less into the reservoir, realized by the position of the first sensor. When this latter is activated by the contact block 54 carried by the shaft 49, the signal emitted and applied on the corresponding input of the circuit for automation and power, this is manifest by the opening of the power supply circuit of the electric motor and thus deactivation of the pump.

According to another embodiment mode, the mechanism for maintaining constant level of the liquid in the reservoir 18 can be made by an additional reservoir, airtight, adjoined to the device and provided in the lower part with an outlet nozzle connected by a conduit to an input nozzle of the liquid that the reservoir 18 contains in the lower part.

The device, in the different embodiment forms as described, can be equipped with several nebulization nozzle heads 1 supplied with liquid to be nebulized from a same reservoir and made of compressed gas from a same source of pressure.

Figure 11:
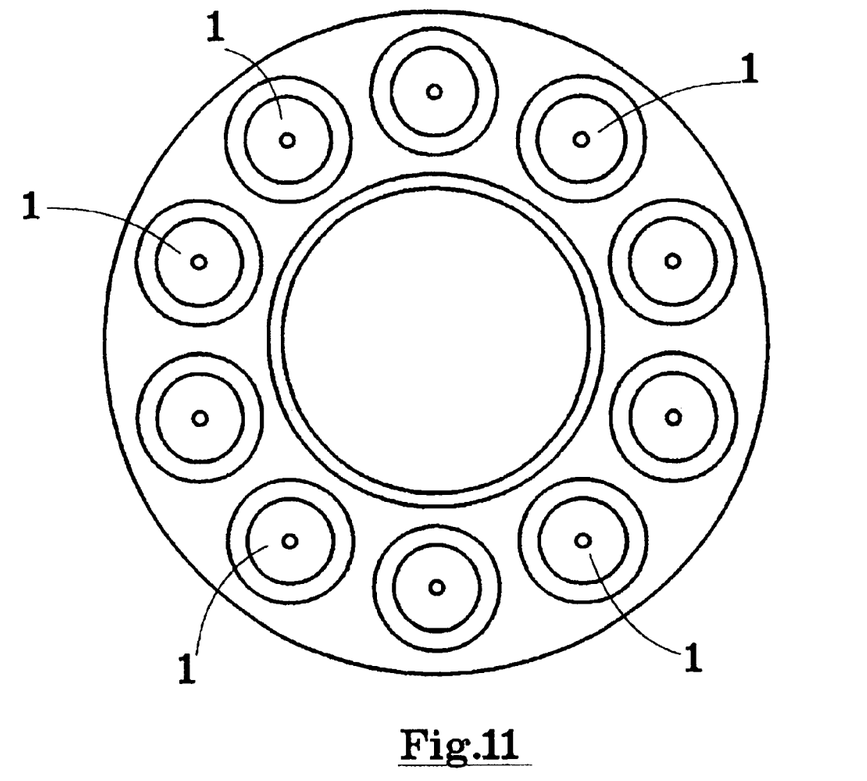
FIG. 11 shows, seen from above, an arrangement of the nebulization nozzle heads according to a first embodiment form.

In FIG. 11, a first arrangement of the nozzle head is shown. According to this embodiment, the nebulization nozzle heads 1 are distributed at regular or irregular intervals along a circle, whose center, for example, will be located on the geometric median vertical axis of the expansion chamber. This arrangement is most especially suited for use with an expansion chamber having a cylindrical form.

Figure 12:
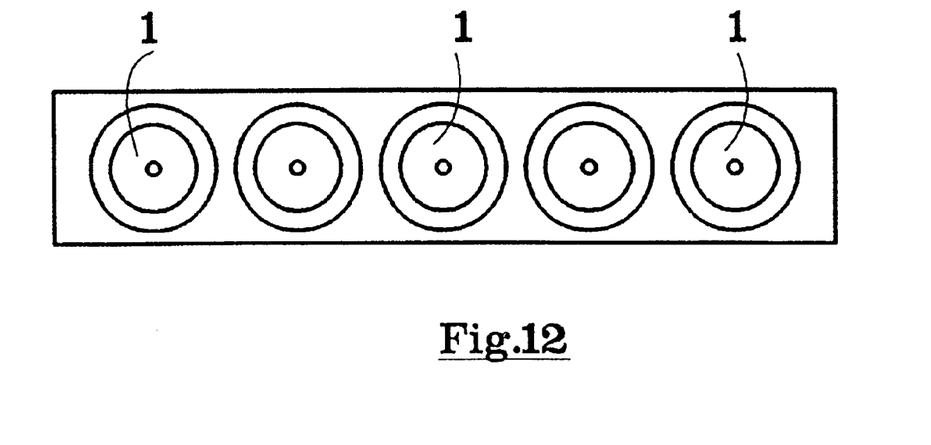
FIG. 12 shows, seen from above, an arrangement of the nebulization nozzle heads according to a second embodiment form.

In FIG. 12, a second arrangement of the nebulization nozzle head is shown. According to this embodiment form, the nebulization nozzle heads are distributed at regular or irregular intervals along a straight line. This arrangement can be used with an expansion chamber having a rectangular cross-section, for a better efficiency, the alignment formed by the nebulization nozzle heads goes along the direction of the length of the this cross-section.

The angle of inclination of each nozzle head relative to a reference can be fixed or even variable.

I claim:

1. A nebulization device comprising:
   a hollow body having a base;
   a nebulization nozzle head mounted on said base, said nozzle head having an open chamber for mixing and fractionating, said open chamber having an outlet nozzle and a first nozzle opposite to said outlet nozzle, a supply hole formed behind said first nozzle, said nozzle bead having an inlet formed therein in communication with said first nozzle;
   a source of compressed gas connected by a supply conduit to said supply hole;
   a reservoir containing a liquid to be nebulized, said reservoir mounted under said hollow body, said nozzle head having said outlet nozzle in communication with an expansion chamber formed in said hollow body coaxial with said open chamber, the liquid being sucked into said open chamber, the liquid being sucked into said open chamber by a partial vacuum created by a gas flow from said first nozzle to said outlet nozzle, the liquid being fractionated and mixed with the gas flow by turbulence in said open chamber, said open chamber having a spreading section in front of said first nozzle, said spreading section having a surface of rotation, said spreading section and a zone of said supply hole being coaxial, said inlet being radial to the air flow across said first nozzle;
   a third nozzle formed downstream of said supply hole at an intersection of said supply hole with said inlet, said first and third nozzles both being in contact with said inlet and spread apart from each other, said first and third nozzles being formed by sharp edges and axially aligned, said outlet nozzle being a conical jet having fine particles in a center thereof and large particles around a periphery thereof, said expansion chamber receiving the large particles emitted by said jet such that the large particles flow by gravity toward a bottom of said expansion chamber, said expansion chamber having a transverse wall opposite said nozzle head, said transverse wall being perpendicular to said open chamber, said transverse wall having a hole at a center thereof passing through said outlet nozzle, said wall having a convex outer side.

2. A nebulization device comprising:
   a hollow body having a base;
   a nebulization nozzle head mounted on said base, said nozzle head having an open chamber for mixing and fractionating, said open chamber having an outlet nozzle and a first nozzle opposite to said outlet nozzle, a supply hole formed behind said first nozzle, said nozzle head having an inlet formed therein in communication with said first nozzle;
   a source of compressed gas connected by a supply conduit to said supply hole;
   a reservoir containing a liquid to be nebulized, said reservoir mounted under said hollow body, said nozzle head having said outlet nozzle in communication with an expansion chamber formed in said hollow body coaxial with said open chamber, the liquid being sucked into said open chamber, the liquid being sucked into said open chamber by a partial vacuum created by a gas flow from said first nozzle to said outlet nozzle, the liquid being fractionated and mixed with the gas flow by turbulence in said open chamber, said open chamber having a spreading section in front of said first nozzle, said spreading section having a surface of rotation, said spreading section and a zone of said supply hole being coaxial, said inlet being radial to the air flow across said first nozzle; and
   a third nozzle formed downstream of said supply hole at an intersection of said supply hole with said inlet, said first and third nozzles both being in contact with said inlet and spread apart from each other, said first and third nozzles being formed by sharp edges and axially aligned, said outlet nozzle being a conical jet having fine particles in a center thereof and large particles around a periphery thereof, said expansion chamber receiving the large particles emitted by said jet such that the large particles flow by gravity toward a bottom of said expansion chamber, said expansion chamber having a blocking wall opposite said nozzle head, said reservoir having a wall positioned above a highest level of the liquid to be nebulized, said wall of said reservoir having an outlet nozzle.

3. A nebulization device comprising:
   a hollow body having a base;
   a nebulization nozzle head mounted on said base, said nozzle head having an open chamber for mixing and fractionating, said open chamber having an outlet nozzle and a first nozzle opposite to said outlet nozzle, a supply hole formed behind said first nozzle, said nozzle head having an inlet formed therein in communication with said first nozzle;
   a source of compressed gas connected by a supply conduit to said supply hole;
   a reservoir containing a liquid to be nebulized, said reservoir mounted under said hollow body, said nozzle head having said outlet nozzle in communication with an expansion chamber formed in said hollow body coaxial with said open chamber, the liquid being sucked into said open chamber, the liquid being sucked into said open chamber by a partial vacuum created by a gas flow from said first nozzle to said outlet nozzle, the liquid being fractionated and mixed with the gas flow by turbulence in said open chamber, said open chamber having a spreading section in front of said first nozzle, said spreading section having a surface of 
rotation, said spreading section and a zone of said supply hole being coaxial, said inlet being radial to the air flow across said first nozzle;

a third nozzle formed downstream of said supply hole at an intersection of said supply hole with said inlet, said first and third nozzles both being in contact with said inlet and spread apart from each other, said first and third nozzles being formed by sharp edges and axially aligned, said outlet nozzle being a conical jet having fine particles in a center thereof and large particles around a periphery thereof, said expansion chamber receiving the large particles emitted by said jet such that the large particles flow by gravity toward a bottom of said expansion chamber, said hollow body being positioned between said reservoir and said expansion chamber, said hollow body having a transversal partition, said transversal partition carrying said nozzle head; and an evacuation means for passing a residual flow of liquid toward said reservoir, said evacuation means extending through said transversal partition, said evacuation means having a lower end located below a minimum level of the liquid in said reservoir, said evacuation means comprising at least one tube engaged within a hole formed in said transversal partition, said partition and said tube separating in airtight relationship to an interior volume of said reservoir and said expansion chamber in an area above a maximum level of the liquid in said reservoir.

4. A nebulization device comprising:

a hollow body having a base;

a nebulization nozzle head mounted on said base, said nozzle head having an open chamber for mixing and fractionating, said open chamber having an outlet nozzle and a first nozzle opposite to said outlet nozzle, a supply hole formed behind said first nozzle, said nozzle head having an inlet formed therein in communication with said first nozzle;

a source of compressed gas connected by a supply conduit to said supply hole;

a reservoir containing a liquid to be nebulized, said reservoir mounted under said hollow body, said nozzle head having said outlet nozzle in communication with an expansion chamber formed in said hollow body coaxial with said open chamber, the liquid being sucked into said open chamber, the liquid being sucked into said open chamber by v partial vacuum created by a gas flow from said first nozzle to said outlet nozzle, the liquid being fractionated and mixed with the gas flow by turbulence in said open chamber, said open chamber having a spreading section in front of said first nozzle, said spreading section having a surface of rotation, said spreading section and a zone of said supply hole being coaxial said inlet being radial to the air flow across said first nozzle;

a third nozzle formed downstream of said supply hole at an intersection of said supply hole with said inlet, said first and third nozzles both being in contact with said inlet and spread apart from each other, said first and third nozzles being formed by sharp edges and axially aligned, said outlet nozzle being a conical jet having fine particles in a center thereof and large particles around a periphery thereof, said expansion chamber receiving the large particles emitted by said jet such that the large particles flow by gravity toward a bottom of said expansion chamber, said body having a partition in a lower part thereof, said source of compressed gas comprising a rigid cannula in communication with said supply hole, said rigid cannula extending through an axial hole formed in said partition, said cannula extending through the base of said reservoir into said reservoir along a direction of movement of said hollow body, said cannula slidable in a bore formed in a wall of a base of said reservoir, said cannula connected to a flexible conduit exterior of said reservoir, said flexible conduit connected to said source of compressed air;

a pump means having an opening for pumping out the liquid from a liquid reserve, said pump means connected by a conduit to the liquid reserve, said pump means having a delivery opening connected by another conduit to said reservoir; and an electric motor means connected to said pump means for actuating said pump means, said electric motor means having two sensors exterior of said reservoir, said two sensors spaced from each other, said two sensors positioned along a path of an activation contact by said cannula.

* * * * *